(12) United States Patent
Prasad et al.

(10) Patent No.: US 8,759,054 B2
(45) Date of Patent: Jun. 24, 2014

(54) DNA LOADED SUPPORTED GOLD NANOPARTICLES, PROCESS FOR THE PREPARATION AND USE THEREOF

(75) Inventors: L.V. Bhagavatula Prasad, Maharashtra (IN); Shanmugham Vijaykumar Periyasamy, Maharashtra (IN); Usharraj Abhilash Othalathara, Maharashtra (IN); Mohammad Khan Bashir, Maharashtra (IN)

(73) Assignee: Council of Scientific & Industrial Research, New Delhi (IN)

( * ) Notice: Subject to any disclaimer, the term of this patent is extended or adjusted under 35 U.S.C. 154(b) by 0 days.

(21) Appl. No.: 13/388,616

(22) PCT Filed: Aug. 3, 2010

(86) PCT No.: PCT/IN2010/000513
§ 371 (c)(1),
(2), (4) Date: Feb. 2, 2012

(87) PCT Pub. No.: WO2011/016053
PCT Pub. Date: Feb. 10, 2011

(65) Prior Publication Data
US 2012/0129223 A1 May 24, 2012

(30) Foreign Application Priority Data
Aug. 4, 2009 (IN) .......................... 1620/DEL/2009

(51) Int. Cl.
C12P 3/00 (2006.01)
C12N 1/16 (2006.01)
C12N 15/63 (2006.01)
C12N 15/64 (2006.01)
B82Y 5/00 (2011.01)
C22C 5/02 (2006.01)

(52) U.S. Cl.
USPC .... 435/168; 435/91.4; 435/320.1; 435/254.1; 977/703; 977/810; 977/906; 420/527

(58) Field of Classification Search
USPC ....................................................... 435/168
See application file for complete search history.

(56) References Cited

U.S. PATENT DOCUMENTS

| 6,537,344 B2 * | 3/2003 | Mukherjee et al. ............. 75/362 |
| 2005/0214916 A1 * | 9/2005 | Absar et al. .................... 435/168 |
| 2005/0239183 A1 | 10/2005 | Mukherjee et al. |

OTHER PUBLICATIONS

Sandhu KK et al. (2002). Gold Nanoparticle-Mediated Transfection of Mammalian Cells. Bioconjugate Chem., v13, p. 3-6.*
Vakarelski I et al. (2007). Penetration of Living Cell Membranes with Fortified Carbon Nanotube Tips. Langmuir, v23, p. 10893-10896.*
Narayanan KB and Sakthivel B (2010). Biological synthesis of metal nanoparticles by microbes. Advances in Colloid and Interface Science. v156(1-2), p. 1-13.*
Morones JR et al. (2005). The bactericidal effect of silver nanoparticles. Nanotechnology, v16, p. 2346-2353.*
Lin XM and Sorensen CM (1999). Ligand-Induced Gold Nanocrystal Superlattice Formation in Colloidal Solution. Chem. Mater., v11, p. 198-202.*
Sivamani E et al. (2009). Protamine-mediated DNA coating remarkably improves bombardment transformation efficiency in plant cells. Plant Cell Rep., v28, p. 213-221.*
Zhang G et al. (2009). Influence of anchoring ligands and particle size on the colloidal stability and in vivo biodistribution of polyetheylene glycol-coated gold nanoparticles in tumor-xenografted mice. Biomaterials, v30, p. 1928-1936.*
Gericke M et al. (2006). Microbial Production of Gold Nanoparticles. Gold Bulletin, v39(1), p. 22-28.*
Vijayakumar PS et al. (2009). Intracellular Biogenic Silver Nanoparticles for the generation of carbon supported antiviral and sustained bactericidal agents. Langmuir, v25(19), 11741-11747.*
Vijayakumar PS et al. (2010). Vice to virtue: Intracellular biogenic nanoparticles for the generation of carbon supported catalysts. Journal of Nanoscience and Nanotechnology, v10, p. 905-911.*
Berthelin J et al. (1990). A bag method to study the release, exchange, fixation and preconcentration of elements from soil minerals. Nutrient Cycling in Terrestrial Ecosystems. Field Methods, Application and Interpretation, ed. by Harrison Ineson and Heal, ISBN=1851663886, p. 26-35.*
Francis Torney et al. Mesoporous silica nanoparticles deliver DNA and chemicals into plants, Apr. 29, 2007, pp. 295-300, vol. 2, No. 5, Nature Nanotechnology May 2007.
Ivan Vakarelski et al. Penetration of living cell membranes with fortified carbon nanotube tips. Oct. 23, 2007, pp. 10893-10896, vol. 23, No. 22, The ACS Journal of Surfaces and Colloids.

* cited by examiner

*Primary Examiner* — Cherie M Stanfield
*Assistant Examiner* — Sean C Barron
(74) *Attorney, Agent, or Firm* — Luedeka Neely Group, PC

(57) ABSTRACT

The present invention relates to DNA loaded gold nanoparticles embedded in sharp carbonaceous carriers useful for higher DNA delivery efficiently into plants. These nanogold embedded carbon matrices are prepared by heat treatment of biogenic intracellular gold nanoparticles. The DNA delivery efficiency is tested on model plants. These materials reveal good dispersion of the transport material, producing a greater number of GUS foci per unit area. The added advantages of the composite carrier are the lower plasmid and gold requirements. Plant cell damage with the prepared carbon supported particles is very minimal and can be gauged from the increased plant regeneration and transformation efficiency compared to that of the commercial micrometer sized gold particles. This can be attributed to the sharp edges that the carbon supports possess, which lead to better piercing capabilities with minimum damage.

10 Claims, 6 Drawing Sheets

Figure 1:
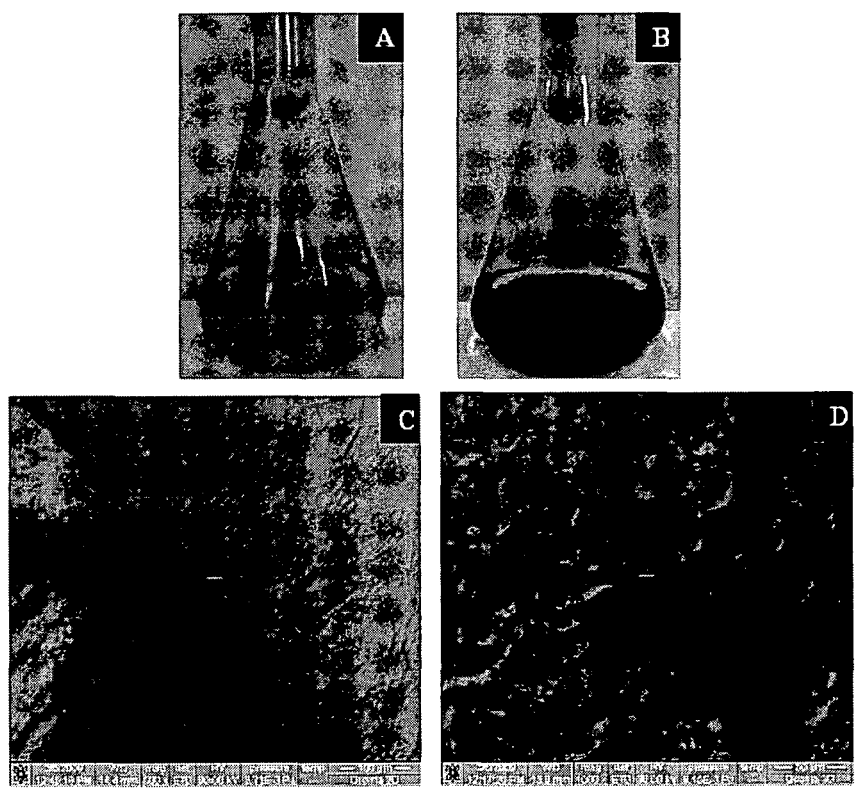

DNA LOADED SUPPORTED GOLD NANOPARTICLES, PROCESS FOR THE PREPARATION AND USE THEREOF

FIELD OF INVENTION

The present invention relates to DNA loaded supported gold nanoparticles, process for the preparation and use thereof. More particularly, the present invention relates to carbon embedded nano gold particles with sharp edges useful for gene delivery. The invention further relates to a process for the preparation of the said carbon embedded nano gold particles with sharp edges and method of transformation of plants using the same. While the carbon support is expected to have the traits like inertness and better piercing capacity, the embedded Au nanoparticles provide the best support to DNA.

BACKGROUND AND PRIOR ART

Genetic manipulation to display the desired trait in biological components has opened up many new avenues. Viral vectors have been identified as successful gene delivery vehicle. Since they have the limitations like acute toxicity, cellular immune response, oncogenicity due to insertional mutagenesis, limited cargo capacity, resistance to repeated infection and production and quality control alternatives, non viral vectors like lipids, polymeric compounds, carbohydrate dendrimers and polypeptide based systems have been demonstrated to be better alternatives. Nanoparticles, especially carbon nanostructures are being studied for gene delivery applications. However, most of the studies are restricted to the animal system or the cell lines. On the other hand non viral vectors for plant systems are relatively underdeveloped, except for a novel method developed by Sanford et al as recited in Nature, 1987 327, 70-73, using a particle gun that employs accelerated DNA coated micro gold projectiles, that deliver DNA into intact plant cells. As an improvement to the micro gold structure, Wang and co-workers synthesized mesoporous silica loaded with nano gold for multiplex gene delivery as published in Nature Nanotech., 2007, 2, 295-300. While the low density mesoporous silica covered with gold was shown to penetrate soft maize embryo, there was no demonstrable data to show penetration of hard embryo like the one of woody tree species.

Recently, a tetrapod sharp structure was reported to deliver DNA into the human cell line mimicking viral vector capsid where the tetrapod's sharp tip carrying the plasmid enters into the cell bringing out necessary transfection; in an article titled "Three dimensional functionalized tetrapodlike ZnO nanostructures for plasmid DNA delivery" by Leng Nie et al in the journal, "Small" 2006, 2, 621-625. Similarly, it is also reported that silicon nano needles (of 200-300 nm diameter) required a force of 0.7-2.0 nN) as compared to a carbon nanotube (of 30-40 nm diameter) that required a lower force (0.1-0.2 nN) to penetrate the plasma membrane by Vakarelski et al in Langmuir, 2007, 23, 10893-10896, that once again highlighted the utility of sharp objects for gene delivery type applications.

It is noteworthy to mention here that ample literature is available on the synthesis of metal nanoparticles by microbes, both intracellularly and extracellularly (reference is drawn to Narayanan, K. B. and Sakthivel, N. 2010. Advances in Colloids and Interface Science. 156 [1-2]: 1-13). However, no report on gene delivery through nanoparticles loaded on sharp edged supports is available, which can not only facilitate DNA transfer to soft tissues but also hard tissues.

Thus, the prior art survey reveals a need for a carrier of genetic material with sharp edges. Further, the carrier should also have adequate capacity to carry the genetic material and the sharpness to penetrate to hard material, but with less damage. The process of preparation of said carriers should be a simple, easy to implement and still fill the gaps in prior arts and needs in the art.

OBJECTS OF THE INVENTION

The main object of the present invention is therefore to provide sharp edged gene carrier composition.

Another object of the present invention is to provide gold nanoparticles embedded in sharp edged supports for gene delivery.

Yet another object of the present invention is to provide a carrier of genetic material having the ability to penetrate hard materials with negligible damage to the material.

Still another object of the present invention is to provide a composite carrier for gene delivery that has low plasmid and gold requirements.

A further object of the present invention is to provide a process for the preparation of DNA loaded supported nano gold particles with sharp edges and method of transformation of plants using the same.

SUMMARY OF THE INVENTION

Envisaging that the combination of a carrier with sharp edges and nano gold could be an important breakthrough in gene gun based transformation, herein we describe the preparation of carbon supported gold nanoparticles using a combination of biochemical/physical/chemical transformations. The particles are prepared by inert heating of the intracellular gold nanoparticles, in situ synthesized by fungus *Aspergillus ochraceus* ITCC 6436 corresponding to ATCC 18500. The intracellular gold nanoparticles heat treated at 600° C. are denoted as HTC-600 Au further in the text for brevity. This matrix supports gold nanoparticles giving the platform for the DNA to bind and provide minimum density for the carrier, to gain threshold velocity in the gene gun to pierce the hard cell wall in plant systems. The Au nanoparticles embedded in the carbon matrix provide the platform to which the DNA can bind. The carbon support clamped the Au nanoparticles and prevented them from leaching during sonication, a step required in DNA coating procedure. On the other hand, in the pure carbon material, the DNA could not be bonded as no gold was present.

Accordingly, the present invention provides DNA loaded supported gold nanoparticles characterized in that the DNA loaded supported nano gold particles having sharp edges as shown in FIG. 2A, curve 2.

The present invention further provides a process for the preparation of DNA loaded supported gold nanoparticles, wherein the steps comprising:

[a] inoculating a microbial culture capable of synthesizing intracellular gold nanoparticles in a nutrient medium and culturing to obtain a biomass;

[b] harvesting the biomass obtained in step [a] followed by washing the biomass with sterilized distilled water under aseptic conditions;

[c] suspending the washed biomass obtained in step [b] in $HAuCl_4$ solution and incubating for 2-3 days followed by washing the biomass with sterilized distilled water under aseptic conditions;

[d] heat treating the washed biomass obtained in step [c] for 6-8 hours in a tubular furnace under inert conditions to obtain the heat treated carbon gold HTC-600 Au;

[e] washing the HTC-600 Au as obtained in step [d] with ethanol;

[f] mixing the ethanol-washed, sterilized HTC-Au-600 with DNA suspended in the XHO buffer (Tris.Cl, NaC-based buffer);

[g] equilibrating the mixture as obtained in step [f] with spermidine and PEG in sequence followed by sonication in 2.5 M $CaCl_2$;

[h] centrifuging the sonicated mixture as obtained in step [g] at 12000 rpm and washing the pellets twice using absolute alcohol and finally resuspending in the required volume of ethanol to obtain DNA loaded supported gold nanoparticles.

BRIEF DESCRIPTION OF THE ACCOMPANYING DRAWINGS

FIG. 1. A: Biomass before incubation with the gold ions.
B: Biomass after incubation with the gold ions
C: Fine micro hyphal thread of the fungus under SEM.
D: Calcined biomass under SEM.

Figure 2:
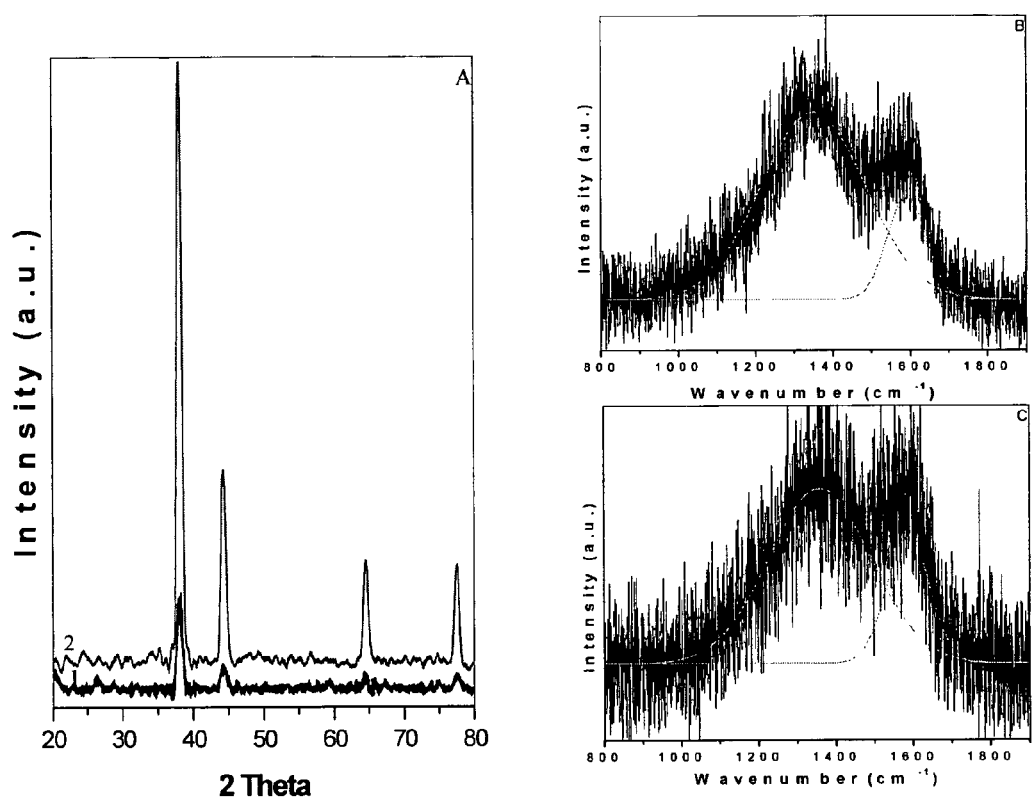

FIG. 2. A: XRD spectrum.
Curve-1: Uncalcined biomass incubated with $1\times10^{-3}$ M $HAuCl_4$;
Curve-2: Heat treated carbon gold at 600° C. (HTC 600-Au).;
B: Raman spectrum of biomass (Sample 1);
C: Raman spectrum of heat treated carbon gold at 600° C. (HTC 600-Au).

Figure 3:
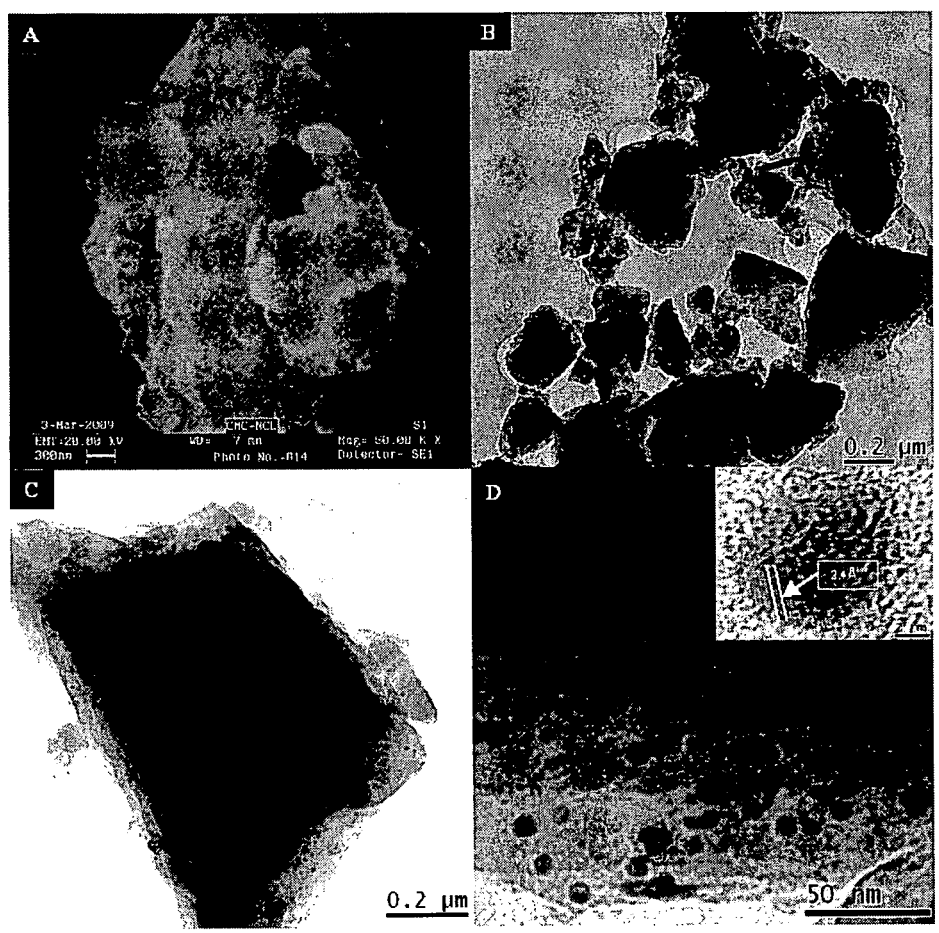

FIG. 3. (A) SEM image of heat treated carbon gold at 600° C. (HTC 600-Au);
(B, C and D): TEM image of heat treated carbon gold at 600° C. (HTC 600-Au). Note the presence of small gold particles plane embedded in carbon matrix as revealed by the TEM images in C and D; Inset D HRTEM image of the gold nanoparticle showing the "d" spacing corresponding to 111 phase of gold.

Figure 4:
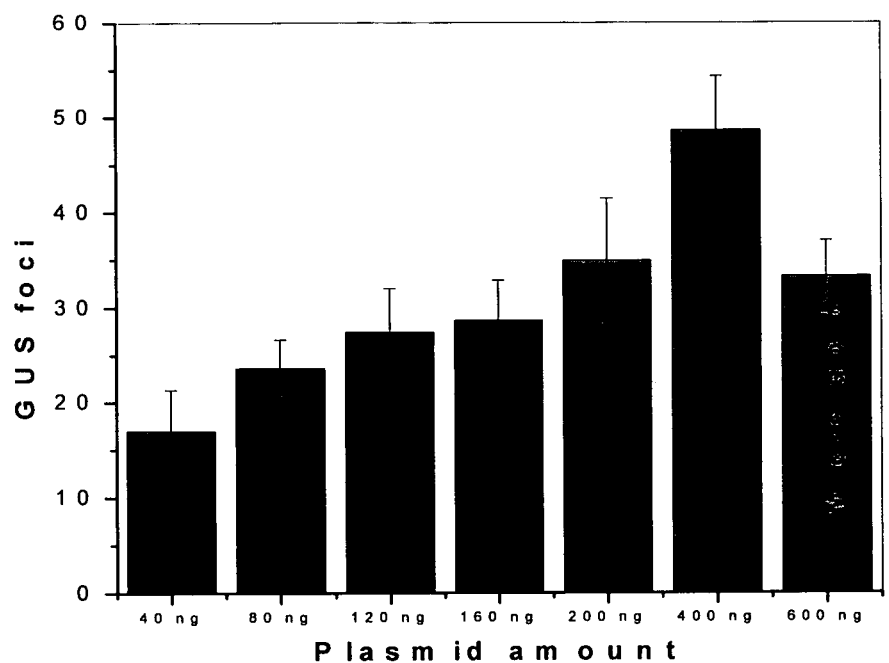

FIG. 4. Standardization of different concentrations of plasmid DNA on 1 mg heat treated carbon gold at 600° C. (HTC 600-Au) to match the number of GUS foci as obtained with specifications for commercial micro gold.

Figure 5:
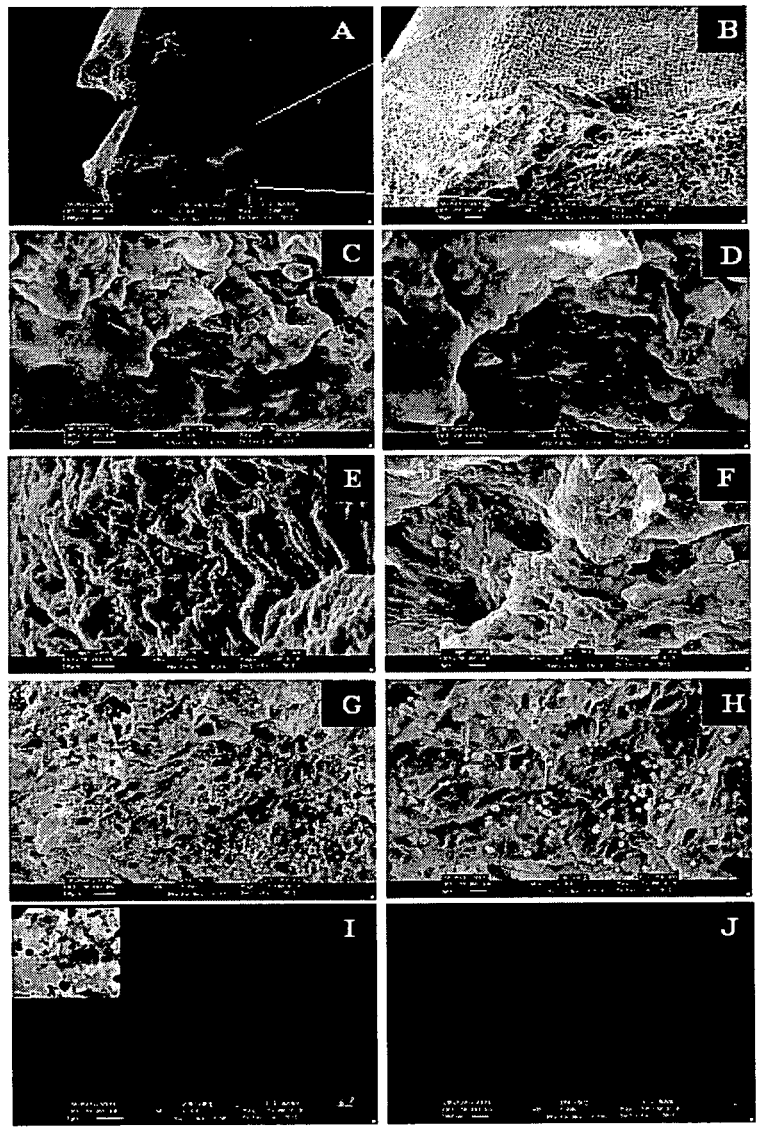

FIG. 5. SEM image of biolistic bombarded *Leucaena* embryo.
A, B, C and D: Embryo at 100, 30, 10 and 3 μm scale;
E and F: Embryo bombarded with HTC 600-Au at 10 and 3 μm scale;
G and H: Embryo bombarded with micro gold particles at 10 and 3 μm scale;
I and J: Embryo without bombardment at 1 μm and 300 nm scale.

Figure 6:
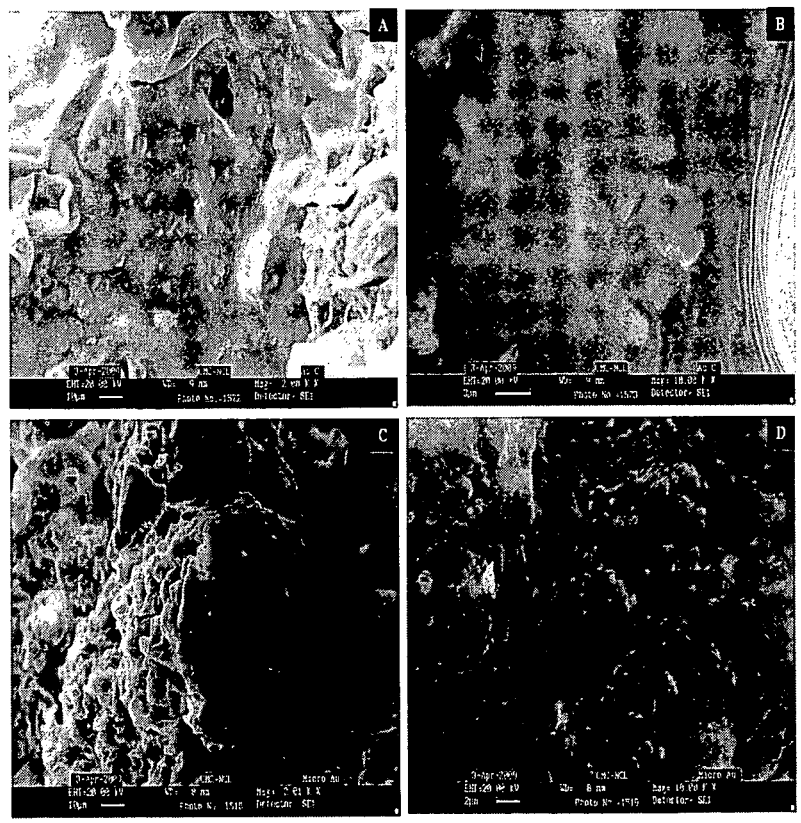

FIG. 6. SEM image of biolistic bombarded rice callus. A and B Callus bombarded with HTC 600-Au; C and D Callus bombarded with micro gold particles.

DETAILED DESCRIPTION OF THE INVENTION

For the purpose of this invention, the expression 'nanogold loaded sharp edged carbon bullets', 'gold nanoparticles supported on sharp carbonaceous sheets' and 'HTC 600-Au' are used interchangeably through out the specification and the same may be appreciated as such by the person skilled in the art.

As described herein the term 'HTC 600-Au' refers to 'heat treated carbon gold at 600° C., prepared by the process of present invention.

In this invention, a composite material comprising gold nanoparticles supported on sharp carbonaceous sheets is described as an alternative material for gene delivery using the gene gun developed by Sanford and coworkers. While the carbon support is expected to be having the required traits such as inertness, better piercing capacity, the embedded gold nanoparticles provide the best support to DNA.

The first step towards the preparation of above composite material involves, the incubation of microbial biomass capable of synthesizing Au nanoparticles intracellularly with gold ions leading to the development of ruby red colour to the biomass indicating the reduction of gold ion into Au nanoparticles inside the cellular matrix. The concentration of the gold precursor to the biomatrix was optimized to get the maximum loading of gold nanoparticles into the biomatrix. Additionally, the concentration of gold obtained after calcinations was found to be consistent across the different batches tested.

In order to ascertain that the composite material HTC-600 Au can function as an efficient DNA delivery agent, the above synthesized HTC-600 Au was coated with DNA using the normal routine procedures specified for micrometer sized gold particles [Bio-Rad Laboratories, Hercules, USA]. Finally, the DNA coated HTC-600 Au was suspended in absolute ethanol and stored at −20 degree C. prior to use. Transformation experiments were carried out using aliquots of the above DNA coated HTC-600 Au with a Biolistic-PDS 100/He system.

Upon standardizing the plasmid DNA delivery to the dicot tree species *Leucaena leucocephala*, it was found that only 200 ng of plasmid DNA loading on HTC 600-Au (heat treated carbon gold at 600° C.) was enough to match the results obtained with the 600 ng of plasmid DNA loaded on commercial abiotic micron gold carriers (FIG. 3B). Therefore, all further studies were carried out with 200 ng plasmid DNA loading on HTC 600-Au. Further, using the particles size distribution (FIG. 2C; inset) and the weight of gold used it was determined that this 200 ng plasmid DNA corresponded to ~0.23 plasmids getting loaded on one gold particle. In comparison, 600 ng of the plasmid loading on micron sized gold corresponded to ~2100 plasmids loaded on each particle. Thus, it is evident that the plasmid DNA are more evenly spread on HTC 600-Au due to the higher surface area and they are efficiently delivered to the desired location.

Accordingly, the present invention discloses a composite material comprising gold nanoparticles supported on sharp carbonaceous sheets.

In an embodiment, the present invention provides a supported carrier composition of optionally a metal, metal ion or metal oxide nanoparticles.

In another embodiment, the supported carrier composition of metal nanoparticles of the invention find use in many areas such as, but not limited to use for DNA delivery, metal ion removal, fuel cell, antibacterial and catalysis.

In yet another embodiment, the supports are selected from carbonaceous, nitrogenous, sulphur, Phosphorous, cellular material, living matter and the like.

In another embodiment, the microorganisms are preferably selected from *Pseudomonas stutzeri* AG 259 ATCC 17588, *Shewanella algae, Plectonema boryanum* UTEX485, *Escherichia coli* DH5α, *Rhodobacter capsulatus, Corynebacterium* p. SH09, *Bacillus* sp., *Lactobacillus* sp., *Verticillium* sp. (AAT-TS-4) (ATCC. 16312), *Trichothecium* sp., *V. luteoalbum, Aspergillus ochraceus* and *Aspergillus flavus*.

In yet another embodiment, the present invention provides a process for the preparation of DNA loaded supported gold nanoparticles, preferably on a carbonaceous support wherein the steps comprising:

a) inoculating the fungal spores in a medium containing maltose-glucose-yeast extract and peptone broth;
b) allowing the spores to germinate to produce hyphal threads for three days at 37° C. to obtain biomass that was harvested followed by washing the biomass with autoclaved MilliQ® water under sterile condition;
c) resuspending the biomass obtained in step (b) in $HAuCl_4$ solution followed by incubation for two days at 37° C. followed by washing with MilliQ® water;
d) heat treating the biomass obtained in step (c) at 600° C. for 6 hours in a tubular furnace under nitrogen flow to obtain the product HTC 600-Au;
e) washing the HTC-600 Au as obtained in step (d) with ethanol and mixing with DNA suspended in the XHO buffer (Tris.Cl, NaC-based buffer);
f) equilibrating the mixture as obtained in step (e) with spermidine and PEG in sequence followed by sonication in 2.5 M $CaCl_2$;
g) centrifuging the sonicated mixture as obtained in step (f) at 12000 rpm and washing the pellets twice using absolute alcohol and finally resuspending in the required volume of ethanol to obtain DNA loaded gold nanoparticles supported on carbonaceous support.

In another embodiment of the invention, the spores are preferably of *Aspergillus ochraceus* ITCC 6436 corresponding to ATCC 18500. The concentration of $HAuCl_4$ solution is preferably $10^{-3}$ Moles.

In still another embodiment, on wet weight basis 60 g of washed biomass was suspended in 200 mL of $10^{-3}$ M $HAuCl_4$. The product was heat treated to get 400 mg of HTC-600 Au.

In yet another embodiment, the carrier composition of the invention is prepared by inert heating of intracellular gold nanoparticles, in situ synthesized by the fungus *Aspergillus ochraceus* ITCC 6436 corresponding to ATCC 18500 as exemplified in example 1. This matrix supports gold nanoparticles giving the platform for the DNA to bind and provide minimum density for the carrier and to gain threshold velocity in the gene gun to pierce the cell wall in plant systems.

In still another embodiment of the present invention, a combination of 1 to 10 mg carrier composition with at least 2 ng DNA per bombardment shows different levels of transformation in different species.

In yet another embodiment of the invention, in order to investigate the carrier composition of the invention for genetically modified cells, studies were conducted on plants of the family Solanaceae, Poaceae and Fabaceae. However, genetically modified cells of the process of the invention are selected from, but not limited to plant species, bacteria, fungi, yeast and mammalian cells.

In a further embodiment, the average regeneration efficiency from the three replicas obtained for tobacco was 41.73 and 38.93% with a transformation efficacy of 14.80 and 12.40% for HTC 600-Au and micro gold respectively. In case of rice, the regeneration efficiency was 26.42 and 23.25% with a transformation efficacy of 9.33 and 8.42% for HTC 600-Au and micro gold respectively. In the case of *Leucaena*, as the regeneration time required is more (6 to 7 months), the putative transgenic plants are still under the process of selection, hence the regeneration and transformation efficiency were not worked out.

In another embodiment, as the carbon matrix forms 95% of the carrier, the amount of gold as well as the DNA used per transformation is reduced according to the present invention. Moreover, the higher transient or stable GUS expression and transformation efficiency observed with the prepared material in the model plant *Nicotiana tobaccum*, monocot *Oryza sativa* and dicot tree species *Leucaena leucocephala* was attributed to the less damage produced by this smaller and sharp edged carrier in comparison to classical 1.0 μm abiotic carriers as proved with SEM studies. The higher ratio of GUS foci to HTC 600-Au payload brings a chance to reduce the percent chimera, which is a serious concern in gene gun approach.

In still another embodiment, the gold particles are in the nano scale providing higher gold surface area for handling more gene cargo. Also, graphite like carbon with the sharp edge can pierce the hard plant cell wall and nuclear membrane and place the gene into the chromatin thread. The SEM images indicate that after the transformation using the gene gun the wound healed very quickly, which is required for efficient transformation.

EXAMPLES

The following examples, which include preferred embodiments, will serve to illustrate the practice of this invention, it being understood that the particulars shown are by way of example and for purpose of illustrative discussion of preferred embodiments of the invention And should not be construed to limit the scope of the present invention.

Example 1

In a typical reaction the isolated fungal spores were inoculated in 500 mL Erlenmeyer flask containing 200 mL of maltose-glucose-yeast extract and peptone broth. The spores of *Aspergillus ochraceus* ITCC 6436 corresponding to ATCC 18500 were allowed to germinate and produce hyphal thread for three days in a shaker (200 rpm) at 37° C. It produced 60 g biomass on wet weight basis that was harvested and three rounds of washing (1000 rpm 15 min) were done with autoclaved Milli-Q® purified water under sterile condition. The biomass was then resuspended in 200 mL of $10^{-3}$ M HAuCl4 followed by incubation in a shaker (200 rpm) for two days at 37° C. The product biomass was washed with Milli-Q® purified water and heat treated (600° C. for 6 hours) in a tubular furnace under nitrogen flow. It gave 400 mg product that was ground finely and characterized. The gold concentration in this sample was analyzed using AAS and found to be ~5 wt %. This sample was denoted as HTC 600-Au. The incubation of fungal biomass with gold ions leading to the development of ruby red colour in the biomass indicated the reduction of gold ion to Au nanoparticles inside the cellular matrix (FIG. 1A and B).

Example 2

The XRD signal of the biomass dried at room temperature and grained to powder (FIG. 2A curve 1); and calcined in inert atmosphere at 600° C. (FIG. 2A curve 2) were recorded. The XRD patterns of the as prepared sample (curve 1) showed a number of Bragg reflections at d values≈2.36, 2.04, 1.45 and 1.23 Å characteristic of the fcc gold. This clearly showed that the nanoparticles are formed just by the treatment of gold ions with the biomass. The peaks in the HTC 600-Au (curve 2) were sharper than those in the samples prepared without heating, indicating an improvement in the crystallinity upon heating.

Example 3

TEM samples of carbon supported HTC 600-Au were prepared by placing drops of their aqueous dispersions over amorphous carbon coated copper grids and allowing the solvent to air dry. Transmission Electron Microscopy (TEM) images were recorded using a Technai $G^2$ F-30 model operated at an accelerating voltage of 300 kV and JEM 2100 instrument operated at 200 kV. The SEM image in FIG. 3A shows a sharp particle made up of many flat sheet like material. This figure was selected to highlight the sharp tips/edges such materials could possess. The TEM image (FIG. 3B) at lower magnification showed the presence of 50 nm Au nanoparticles embedded in the carbon matrix with sharp edges. In the FIG. 3C apart from the few 50 nm particles plenty of 5 nm particles spread throughout the carbon sheet is observed. Still closer view of the carbon in the FIG. 3D showed wavy edge, showing bundle of sheet arrangement with one sheet getting protruded to form a sharp edge. The HRTEM image (inset FIG. 3D) of one of the isolated particle shows a "d" spacing of 2.4 Å that matches with the lattice spacing 2.36 Å of (111) gold plane.

Example 4

Raman spectra were measured in the backscattering configuration using a 632.8-nm HeNe laser excitation. The scattered light was analyzed in a Jobin-Yvon HR800 spectrometer equipped with a charge-coupled array detector and a holographic notch filter. To avoid laser damage to the sample the experiments were conducted at low laser powers (2 W/cm$^2$). The Raman signals of the HTC 600-Au are plotted in FIG. 2C. The curves show features characteristic of disordered carbon with peaks at ~1590 cm$^{-1}$ and ~1350 cm$^{-1}$ that are designated as G and D peak respectively. The data was deconvoluted and fitted to two Gaussian peaks. From the intensity of the peak at 1365 and 1590 cm$^{-1}$ the graphite in-plane domain size ($L_a$) value was determined to be 1.35 nm in HTC 600-Au,[12] as compared to 0.90 nm in the pure carbon sample without gold nanoparticles. The inplane size of 1.35 nm in HTC 600-Au still suggested the presence of an amorphous carbon matrix.

Example 5

The gold concentrations were measured with a Chemito-Atomic Absorption Spectrometer (AAS) 201 with a gold hollow cathode lamp. Scanning Electron Microscopic (SEM) images were recorded from Leica Stereoscan 440 model.

Example 6

Tobacco (*N. tabaccum* var. Anand 119) plants were grown in vitro on basal Murashige and Skoog medium (MS medium 1962) in absence of any plant growth regulators. Fresh leaves from two months old plants were used as explants and were cut into pieces of about 5 mm$^2$ and inoculated in MS basal medium (pH 5.8) with 1.4% agar, supplemented with 2% sucrose, 0.8% 6-benzyl amino purine (BAP) and alpha-napthalene acetic acid (NAA) for callus induction under darkness at 25±2° C. in a growth incubator. The selected embryogenic calli derived from leaf explants, were bombarded twice with HTC-600Au after arranging at the center of a 90 mm diameter Petri-plate using rupture discs with 900 pounds per square inch (psi) specification with 25 inches of Hg vacuum at an interval of 4 hours. After two days of incubation under darkness the bombarded calli were shifted to differentiating media containing basal MS medium, B5 vitamins, 1 mg/L BAP, 0.1 mg/L NAA, 30 g/L sucrose, 4 g/L phytagel for a week and later transferred to the same medium containing plant selection marker kanamycin 100 mg/L concentration. The putative transgenic plants, which survived three rounds of selection, were analyzed.

Manually dehusked rice (local elite indica cultivar IR64) seeds were surface sterilized with 70% ethanol for 3 min followed by 1.5% (v/v) sodium hypochlorite for 10-15 min and washed 5-7 times with sterile distilled water. Then, the sterilized seeds were plated onto MS medium containing 2.5 mg/L 2,4-D (Callus induction medium) and incubated in dark at 25±2° C. for 3 weeks. 50 friable embryogenic calli were counted and placed at the center of a 90 mm diameter Petri plate with callus induction medium containing osmotica (Callus induction medium supplemented with 36.4 g/L mannitol and 36.4 g/L sorbitol), 4 hours prior to the first shooting using PDS-1000/He Biolistic Particle Delivery System. The explants were bombarded twice using rupture discs as done before. After forty-eight hours of the second bombardment, the calli were directly transferred on to MS callus induction medium containing 50 mg/L hygromicin B, and incubated at 25±2° C. for 15-18 days. Actively proliferating calli were subcultured onto a fresh selection medium thrice at 15-18 days interval. The proliferating embryogenic calli after 3 rounds of selection on hygromycin B were transferred onto an MS regeneration medium (MS medium supplemented with BAP and NAA (Sigma, USA) 3 mg/L and 0.5 mg/L respectively). The calli were cultured for 16 hours in light (110-130 mM/m$^2$/s) and 8 hours in dark at 25° C. till shoot established. Emerging shoots were transferred to MS rooting medium (half-strength MS basal salts, MS vitamins and 15 g/L sucrose) containing 30 mg/L hygromycin B.

Example 7

The seeds of *Leucaena leucocephala* (Lead tree, white popinac, subabul) a perennial leguminous tree species taken out from the pods were surface-sterilized with 1.5% (v/v) sodium hypochlorite solution for 10-15 minutes, followed by 4 washes with sterile water.

The immature embryos were isolated aseptically using a pair of sharp, sterile forceps and plated with their shoot apex facing up in the center of a 90 mm diameter Petri plate containing regeneration media (½ MS+Thia Dia Zuron) (0.5 mg/L). The embryos were bombarded as done before and kept under darkness for two days. After growing the embryos on the above regeneration media without selection for one week, they were subjected to three rounds of selections in the same regeneration medium containing Kanamycin 100 mg/L, at an interval of 15 days. The plants, which survived three rounds of selection on Kanamycin 200 mg/L, were shifted to ½ MS with Cytokinin, 2ip (2-isopentenyl adenine) at 0.5 mg/L to enhance elongation of transformed shoots.

In all the above examples, plant transformation was confirmed using polymerase chain reaction. The bombarded tissues were examined with the SEM, to visualize the damage and the penetration efficiency. FIG. 4 reveals that only 200 ng of plasmid is enough to match the results of the 600 ng classical abiotic micron gold carriers used in plant transformation. Also it was found that on increasing the DNA concentration per unit of HTC 600-Au still higher levels of GUS expressing foci can be achieved, which can be optimized and very well used for other plant transformation systems.

Thus, it can be inferred that the sharp edged supported Au nanoparticles produced by simple heat treatment of intracellular biogenic nanoparticles proved to be a better plant transformation abiotic carrier than the commercially available micrometer sized gold particles. This unravels a unique application for the intracellularly synthesized nanoparticles, which otherwise have no application unless the nanoparticles are isolated from the matrix.

Advantages of the Invention

The advantages of the composite that the present invention provides are as follows:

As the gold particles are in the nano scale higher gold surface area is obtained, hence more gene cargo can be handled.

Since gold is known to support high DNA packing density it might give better transformation efficiency and low nuclease degradation.

The embedded gold also improves the density of the composite thus enabling it to gain the necessary threshold velocity.

Moreover, graphite like carbon with the sharp edge can pierce the hard plant cell wall and nuclear membrane and place the gene into the chromosomal site. The SEM images indicate that after transformation the wound on the cell walls/nuclear membrane healed very quickly, which is required for efficient transformation.

We claim:

1. Gold nanoparticles on a sharp edge support and having DNA loaded thereon, said nanoparticles being made by a process comprising:
   [a] inoculating a microbial culture capable of synthesizing intracellular gold nanoparticles in a nutrient medium and culturing to obtain a biomass;
   [b] harvesting the biomass obtained in step [a] followed by washing the biomass with sterilized distilled water under aseptic conditions;
   [c] suspending the washed biomass obtained in step [b] in HAuCl$_4$ solution and incubating for 2-3 days followed by washing the biomass with sterilized distilled water under aseptic conditions;
   [d] heat treating the washed biomass obtained in step [c] for 6-8 hours in a tubular furnace under inert conditions to obtain the heat treated carbon gold HTC-600 Au;
   [e] washing the HTC-600 Au as obtained in step [d] with ethanol;
   [f] mixing the ethanol-washed, sterilized HTC-Au-600 with DNA suspended in the XHO buffer (Tris.Cl, NaC-based buffer);
   [g] equilibrating the mixture as obtained in step [f] with spermidine and PEG in sequence followed by sonication in 2.5 M CaCl$_2$;
   [h] centrifuging the sonicated mixture as obtained in step [g] at 12000 rpm and washing the pellets twice using absolute alcohol and finally resuspending in the required volume of ethanol to obtain the DNA loaded supported gold nanoparticles.

2. The gold nanoparticles of claim 1, wherein the supports are selected from carbonaceous, nitrogenous, sulphur, phosphorous, cellular material, and living matter.

3. The gold nanoparticles of claim 1, wherein the support is carbonaceous.

4. A process for the preparation of DNA loaded supported gold nanoparticles on a sharp-edged support, wherein the steps comprise:
   [a] inoculating a microbial culture capable of synthesizing intracellular gold nanoparticles in a nutrient medium and culturing to obtain a biomass;
   [b] harvesting the biomass obtained in step [a] followed by washing the biomass with sterilized distilled water under aseptic conditions;
   [c] suspending the washed biomass obtained in step [b] in HAuCl$_4$ solution and incubating for 2-3 days followed by washing the biomass with sterilized distilled water under aseptic conditions;
   [d] heat treating the washed biomass obtained in step [c] for 6-8 hours in a tubular furnace under inert conditions to obtain the heat treated carbon gold HTC-600 Au;
   [e] washing the HTC-600 Au as obtained in step [d] with ethanol;
   [f] mixing the ethanol-washed, sterilized HTC-Au-600 with DNA suspended in the XHO buffer (Tris.Cl, NaC-based buffer);
   [g] equilibrating the mixture as obtained in step [f] with spermidine and PEG in sequence followed by sonication in 2.5 M CaCl$_2$;
   [h] centrifuging the sonicated mixture as obtained in step [g] at 12000 rpm and washing the pellets twice using absolute alcohol and finally resuspending in the required volume of ethanol to obtain DNA loaded supported gold nanoparticles on a sharp-edged support.

5. The process of claim 4, wherein the microorganisms are selected from the group consisting of Pseudomonas stutzeri AG 259 ATCC 17588, *Shewanella algae, Plectonema boryanum* UTEX485, *Escherichia coli* DH5α, *Rhodobacter capsulatus, Corynebacterium* p. SH09, *Bacillus* sp., *Lactobacillus* sp., *Verticillium* sp. (AAT-TS- 4) (ATCC. 16312), *Trichothecium* sp., *V. luteoalbum, Aspergillus ochraceus* and *Aspergillus flavus*.

6. The process of claim 4, wherein the microorganism comprises *Aspergillus ochraceus* ITCC 6436 corresponding to ATCC 18500.

7. The process of claim 4, wherein the concentration of HAuCl4 solution is about $10^{-3}$ Moles.

8. A process for the preparation of DNA loaded supported gold nanoparticles on a carbonaceous support having sharp edges wherein the steps comprise:
   (i) inoculating fungal spores of *Aspergillus ochraceus* ITCC 6436 corresponding to ATCC 18500 in a medium containing maltose-glucose-yeast extract and peptone broth;
   (ii) allowing the spores to germinate to produce hyphal threads for three days at 37° C. to obtain biomass that was harvested followed by washing the biomass with autoclaved purified water under sterile condition;
   (iii) re-suspending the biomass obtained in step (ii) in HAuCl$_4$ solution followed by incubation for two days at 37° C. followed by washing with purified water;
   (iv) heat treating the biomass obtained in step (iii) at 600° C. for 6 hours in a tubular furnace under nitrogen flow to obtain the product HTC 600-Au;
   (v) washing the HTC-600 Au as obtained in step (iv) with ethanol and mixing with DNA suspended in the XHO buffer (Tris.Cl, NaC-based buffer);
   (vi) equilibrating the mixture as obtained in step (v) with spermidine and PEG in sequence followed by sonication in 2.5 M CaCl$_2$;
   (vii) centrifuging the sonicated mixture as obtained in step (vi) at 12000 rpm and washing the pellets twice using absolute alcohol and finally re-suspending in the required volume of ethanol to obtain DNA loaded gold nanoparticles supported on carbonaceous support having sharp edges.

9. Gold nanoparticles on a carbonaceous support having sharp edges and having DNA loaded thereon, said nanoparticles being made by a process of comprising:

(i) inoculating fungal spores of *Aspergillus ochraceus* ITCC 6436 corresponding to ATCC 18500 in a medium containing maltose-glucose-yeast extract and peptone broth;

(ii) allowing the spores to germinate to produce hyphal threads for three days at 37° C. to obtain biomass that was harvested followed by washing the biomass with autoclaved purified water under sterile condition;

(iii) re-suspending the biomass obtained in step (ii) in $HAuCl_4$ solution followed by incubation for two days at 37° C. followed by washing with purified water;

(iv) heat treating the biomass obtained in step (iii) at 600° C. for 6 hours in a tubular furnace under nitrogen flow to obtain the product HTC 600-Au;

(v) washing the HTC-600 Au as obtained in step (iv) with ethanol and mixing with DNA suspended in the XHO buffer (Tris.Cl, NaC-based buffer);

(vi) equilibrating the mixture as obtained in step (v) with spermidine and PEG in sequence followed by sonication in 2.5 M $CaCl_2$;

(vii) centrifuging the sonicated mixture as obtained in step (vi) at 12000 rpm and washing the pellets twice using absolute alcohol and finally re-suspending in the required volume of ethanol to obtain gold nanoparticles supported on carbonaceous support having sharp edges.

10. A method of delivering a gene to a chromosomal site of a plant cell using gold nanoparticles on a carbonaceous support having sharp edges comprising piercing the cell wall and nuclear membrane of the plant with the nanopartcles containing the gene, wherein the nanoparticles are made according to a process comprising:

(i) inoculating fungal spores of *Aspergillus ochraceus* ITCC 6436 corresponding to ATCC 18500 in a medium containing maltose-glucose-yeast extract and peptone broth;

(ii) allowing the spores to germinate to produce hvphal threads for three days at 37° C. to obtain biomass that was harvested followed by washing the biomass with autoclaved purified water under sterile condition;

(iii) re-suspending the biomass obtained in step (ii) in $HAuCl_4$ solution followed by incubation for two days at 37° C. followed by washing with purified water;

(iv) heat treating the biomass obtained in step (iii) at 600° C. for 6 hours in a tubular furnace under nitrogen flow to obtain the product HTC 600-Au;

(v) washing the HTC-600 Au as obtained in step (iv) with ethanol and mixing with the gene suspended in the XHO buffer (Tris.Cl, NaC-based buffer);

(vi) equilibrating the mixture as obtained in step (v) with spermidine and PEG in sequence followed by sonication in 2.5 M $CaCl_2$;

(vii) centrifuging the sonicated mixture as obtained in step (vi) at 12000 rpm and washing the pellets twice using absolute alcohol and finally re-suspending in the required volume of ethanol to obtain gold nanoparticles supported on carbonaceous support having sharp edges.

* * * * *